(12) United States Patent
Vijayakumar et al.

(10) Patent No.: US 6,784,988 B2
(45) Date of Patent: Aug. 31, 2004

(54) APPARATUS AND PROCESS FOR ANALYZING A STREAM OF FLUID

(75) Inventors: Rajagopal Vijayakumar, Liverpool, NY (US); Sylvain Dominique Masset, Seigy (FR)

(73) Assignee: Hamilton Associates, Inc., Owings, MD (US)

(*) Notice: Subject to any disclaimer, the term of this patent is extended or adjusted under 35 U.S.C. 154(b) by 17 days.

(21) Appl. No.: 10/196,272

(22) Filed: Jul. 17, 2002

(65) Prior Publication Data

US 2004/0012777 A1 Jan. 22, 2004

(51) Int. Cl.[7] .......................... G01N 21/01; G01J 31/14
(52) U.S. Cl. ........................................ 356/244; 250/574
(58) Field of Search ................................. 356/244, 246, 356/445–448; 250/574, 576, 227.11–227.24, 341.2, 341.8, 339.07, 339.09, 339.11, 339.12

(56) References Cited

U.S. PATENT DOCUMENTS

| | | | |
|---|---|---|---|
| 3,647,304 A | * | 3/1972 | Emmel et al. ............... 356/246 |
| 3,740,155 A | * | 6/1973 | Keller et al. ................ 356/409 |
| 4,050,450 A | * | 9/1977 | Polanyi et al. .............. 600/332 |
| 4,071,298 A | * | 1/1978 | Falconer ...................... 356/73 |
| 4,497,577 A | * | 2/1985 | Sato et al. ................... 356/336 |
| 4,529,306 A | | 7/1985 | Kilham et al. |
| 4,662,749 A | | 5/1987 | Hatton et al. |
| 4,693,602 A | * | 9/1987 | Wyatt et al. ................. 356/336 |
| 4,710,025 A | * | 12/1987 | Wyatt et al. ................. 356/343 |
| 4,808,813 A | | 2/1989 | Champetier |
| 5,077,481 A | * | 12/1991 | Hoult .......................... 250/576 |
| 5,084,614 A | | 1/1992 | Berkner |
| 5,089,714 A | * | 2/1992 | Ludlow et al. .............. 250/574 |
| 5,140,463 A | | 8/1992 | Yoo et al. |
| 5,155,549 A | | 10/1992 | Dhadwal |
| 5,313,542 A | | 5/1994 | Castonguay |
| 5,407,638 A | * | 4/1995 | Wang ....................... 422/82.09 |
| 5,418,615 A | * | 5/1995 | Doyle ......................... 356/436 |
| 5,432,601 A | * | 7/1995 | Tanaka et al. ............... 356/246 |
| 5,471,299 A | * | 11/1995 | Kaye et al. .................. 356/336 |
| 5,526,112 A | | 6/1996 | Sahagen |
| 5,610,712 A | | 3/1997 | Schmitz et al. |
| 5,694,206 A | * | 12/1997 | Curtiss ......................... 356/72 |
| 5,731,875 A | * | 3/1998 | Chandler et al. ............ 356/336 |
| 5,751,422 A | | 5/1998 | Mitchell |
| 5,815,264 A | * | 9/1998 | Reed et al. .................. 356/336 |
| 6,016,095 A | | 1/2000 | Herbert |
| 6,043,895 A | * | 3/2000 | Masterson et al. .......... 356/436 |
| 6,081,322 A | | 6/2000 | Barbour |
| 6,137,108 A | * | 10/2000 | DeThomas et al. ..... 250/339.07 |
| 6,166,806 A | | 12/2000 | Tjin |
| 6,288,783 B1 | * | 9/2001 | Auad .......................... 356/410 |
| 6,490,530 B1 | * | 12/2002 | Wyatt .......................... 702/24 |

* cited by examiner

*Primary Examiner*—Michael P. Stafira
(74) *Attorney, Agent, or Firm*—Merek, Blackmon & Voorhees, LLC

(57) ABSTRACT

An analyzing probe for insertion into numerous different environments to determine at least one characteristic of particulate matter suspended in a fluid stream of a test sample. Preferably, the analyzing probe includes a minimal amount of optical elements such as lenses that are subjected to the conditions of the environment of the fluid stream to be tested. Further, the analyzing probe is preferably designed so that it can be readily manufactured, operated and installed by relatively unskilled laborers.

32 Claims, 5 Drawing Sheets

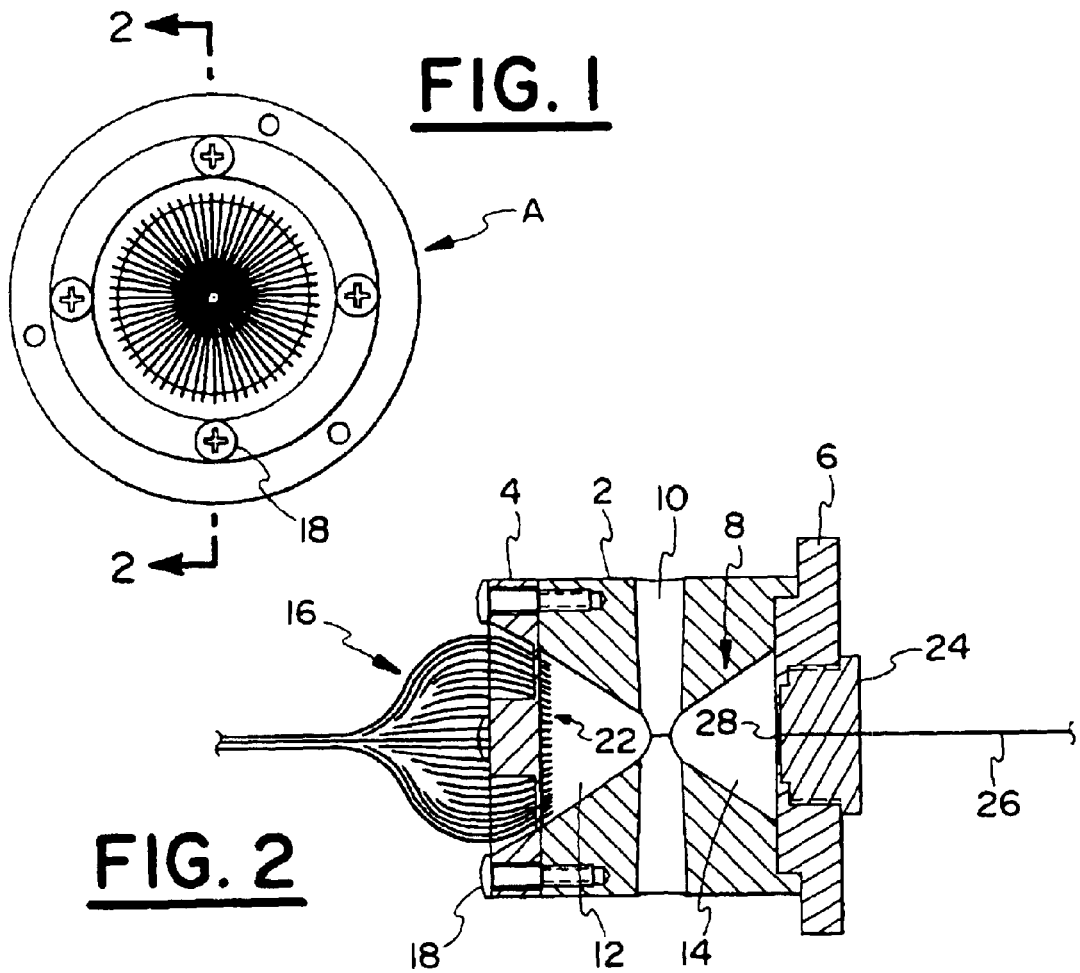
FIG. 1
FIG. 2
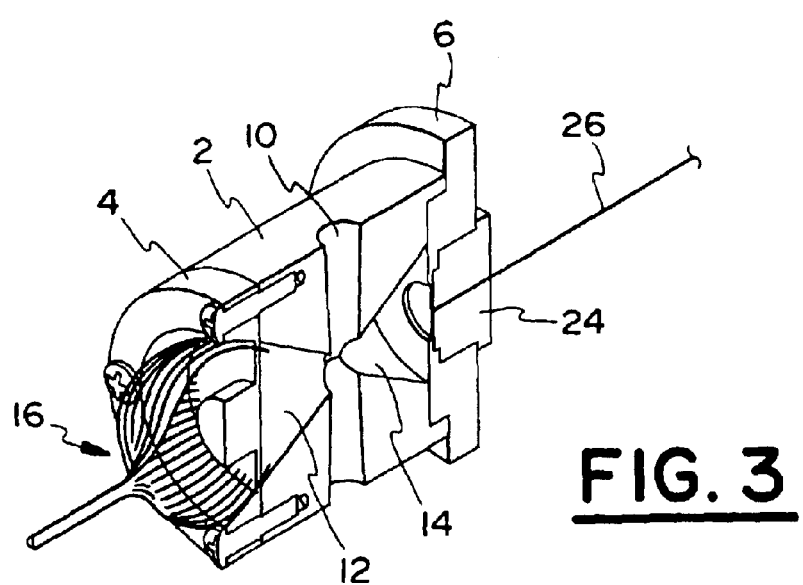
FIG. 3

APPARATUS AND PROCESS FOR ANALYZING A STREAM OF FLUID

FIELD OF THE INVENTION

The present invention is directed to devices and processes used to detect particles in a fluid (i.e., liquid or gas) stream. More specifically, a fluid stream to be tested is subjected to electromagnetic radiation at a sensing region. Particles in the fluid stream cause the electromagnetic radiation to scatter. The electromagnetic radiation affected by the particles in the fluid stream being tested is processed to identify characteristics of the particles including but not limited to particle size, type, distribution and/or concentration.

BACKGROUND OF THE INVENTION

Various devices have been used to test fluid streams to determine characteristics of particles in the fluid stream including particle size, type, distribution or concentration. These devices typically include a light source for generating electromagnetic radiation with a particular wavelength and an optical coupler for transmitting the light to a sensing region. The light illuminating the fluid stream is scattered by the particles suspended in the fluid stream. The scattered light is collected and transmitted to a processing element for analysis to determine various characteristics of the particles. Optical elements including lenses are commonly used to focus the light illuminating the fluid stream. Also, various optical elements such as lenses are used to focus the collected light.

Prior particle analyzing devices have employed a multitude of components and/or required significant adaptation of the environment to be tested to deploy the particle analyzer to test a given fluid stream. The complexity of these prior known devices has necessitated the use of very skilled laborers to manufacture, operate and deploy known particle analyzers to analyze particles in a given fluid stream. It is therefore desirous to develop a particle analyzer that is simple in construction to enable relatively unskilled laborers to manufacture, operate and deploy the particle analyzer to analyze particles in a given fluid stream.

Prior particle analyzing devices have often used a probe or transmitter of one sort or another to transmit light of a specified wavelength to a sensing region remote from the probe, i.e., the area or region where light scattering occurs is outside the light transmitting probe. Examples of such prior known devices are disclosed in U.S. Pat. Nos. 5,751,422; 5,731,875; 4,662,749; 5,526,112; 5,155,549; 5,084,614; and, 5,313,542. These prior devices are disadvantageous, inter alia, because the remote location of the scattering region or chamber makes it more difficult to control and monitor the test fluid and the light used to irradiate the test fluid. Further, an additional component is often required through which the fluid stream to be detected is passed for testing. Accordingly, the complexity and expense of the analyzing system is disadvantageously increased.

Prior known particle analyzers have suffered greatly in accuracy and durability due to their deployment in hazardous test environments. Such hazardous environments subject the particle analyzer to extremely high pressures, temperatures and/or highly corrosive conditions. Prior known particle analyzers have deployed optical elements such as lenses and other components directly into the hazardous test environment. By deploying optical elements directly into the hazardous environment, the accuracy and durability of the prior known particle analyzers have been compromised.

Some prior known particle analyzers are constructed with separate housings for the light transmitting element and the light collecting element. Examples of such prior known particle analyzers are shown in U.S. Pat. Nos. 5,313,542; 6,016,195; and 5,751,422. These constructions are disadvantageous because the additional component requires further adaptation of the environment in which the particle analyzer is deployed. Moreover, the additional component adds to the complexity and expense of the particle analyzer.

OBJECTS AND SUMMARY OF THE INVENTION

An object of a preferred embodiment of the present invention is to provide a novel and unobvious apparatus and process for analyzing a stream of fluid to determine one or more characteristics of particles suspended in the fluid stream.

Another object of a preferred embodiment of the present invention is to provide an apparatus for analyzing a fluid stream that can readily be deployed in an environment with only minimal adaptation of the environment.

Yet another object of one preferred embodiment of the present invention is provide an apparatus for analyzing a fluid stream that can be used in a hazardous environment without any appreciable degradation in the accuracy of the apparatus.

A further object of a preferred embodiment of the present invention is to provide an apparatus for analyzing a fluid stream that can readily direct electromagnetic radiation to a point in a scattering chamber without the use of lenses.

Still a further object of a preferred embodiment of the present invention is to provide an apparatus for analyzing a fluid stream that is relatively easy to manufacture.

Yet still a further object of a preferred embodiment of the present invention is to provide an apparatus for analyzing a fluid stream that is relatively easy to operate and deploy in the field.

It must be understood that no one embodiment of the present invention need include all of the aforementioned objects of the present invention. Rather, a given embodiment may include one or none of the aforementioned objects. Accordingly, these objects are not to be used to limit the scope of the claims of the present invention.

In summary, one embodiment of the present invention is directed to an apparatus for analyzing a stream of fluid. The apparatus includes an analyzing probe adapted to be inserted into a hazardous environment to analyze a stream of fluid. The analyzing probe has a substantially tubular housing. The substantially tubular housing has a longitudinal axis and an exterior surface. The apparatus further includes a scattering chamber and a fluid passageway. The fluid passageway is in fluid communication with the scattering chamber to direct a stream of fluid to be tested into the scattering chamber. The scattering chamber is disposed in the substantially tubular housing of the analyzing probe. At least a portion of the fluid passageway extends at a first angle to the longitudinal axis and between the exterior surface of the substantially tubular housing and the scattering chamber. The apparatus further includes at least one transmitting optical fiber for transmitting electromagnetic radiation to the scattering chamber and at least one collecting optical fiber for collating electromagnetic radiation from the scattering chamber for analysis.

Another embodiment of the present invention is directed to an apparatus for analyzing a stream of fluid. The apparatus includes an analyzing probe to analyze a stream of fluid. The analyzing probe includes a housing having a longitudinal axis. The analyzing probe further includes a scattering chamber and a fluid passageway. The fluid passageway is in fluid communication with the scattering chamber to direct a stream of fluid to be tested into the scattering chamber. The apparatus further includes at least first and second transmitting optical fibers to transmit electromagnetic radiation to the scattering chamber. The first and second transmitting optical fibers are disposed at an angle to the longitudinal axis such that electromagnetic radiation transmitted by the first and second transmitting optical fibers is directed to approximately the same point in the scattering chamber thereby obviating the need for a lens for focusing the electromagnetic radiation to approximately a single point. The apparatus further includes at least one collecting optical fiber for colleting electromagnetic radiation from the scattering chamber for analysis.

A further embodiment of the present invention is directed to an apparatus for analyzing a stream of fluid. The apparatus includes an analyzing member adapted to be inserted into a hazardous environment to analyze a stream of fluid. The analyzing member includes a housing. The apparatus further includes a chamber and a fluid passageway. The fluid passageway is in fluid communication with the scattering chamber to direct a stream of fluid to be tested into the scattering chamber. The scattering chamber is disposed in the housing. The apparatus further includes at least one transmitting optical fiber to transmit electromagnetic radiation to the scattering chamber and at least one collecting optical fiber for collecting electromagnetic radiation from the scattering chamber for analysis. A reflecting member is disposed in the housing for redirecting electromagnetic radiation transmitted by the at least one transmitting optical fiber to the scattering chamber.

Still another embodiment of the present invention is directed to an apparatus for analyzing a stream of fluid. The apparatus includes an analyzing member adapted to be inserted into an environment to analyze a stream of fluid. The analyzing member includes a substantially tubular housing having first and second sections. The first section includes an inner member and an outer member. The apparatus further includes a scattering chamber and a fluid passageway. The fluid passageway is in fluid communication with the scattering chamber to direct a stream of fluid to be tested into the scattering chamber. The scattering chamber is formed in the inner member of the first section of the housing. The apparatus further includes a plurality of transmitting optical fibers to transmit electromagnetic radiation to the scattering chamber and at least one collecting optical fiber for colleting electromagnetic radiation from the scattering chamber for analysis.

BRIEF DESCRIPTION OF THE DRAWINGS

FIG. 1 is a side elevational view of an apparatus formed in accordance with the most preferred embodiment of the present invention.

FIG. 2 is a cross-sectional view of the apparatus depicted in FIG. 1 taken along lines 2—2.

FIG. 3 is a perspective view of a portion of the apparatus depicted in FIG. 1.

DETAILED DESCRIPTION OF THE PREFERRED EMBODIMENT OF THE INVENTION

The most preferred form of the invention will now be described with reference to FIGS. 1–8. The appended claims are not limited to the most preferred embodiment and no term used herein is to be given a meaning other than its ordinary meaning unless accompanied by a statement that the term "as used herein is defined as follows".

FIGS. 1 Through 4

Figure 4:
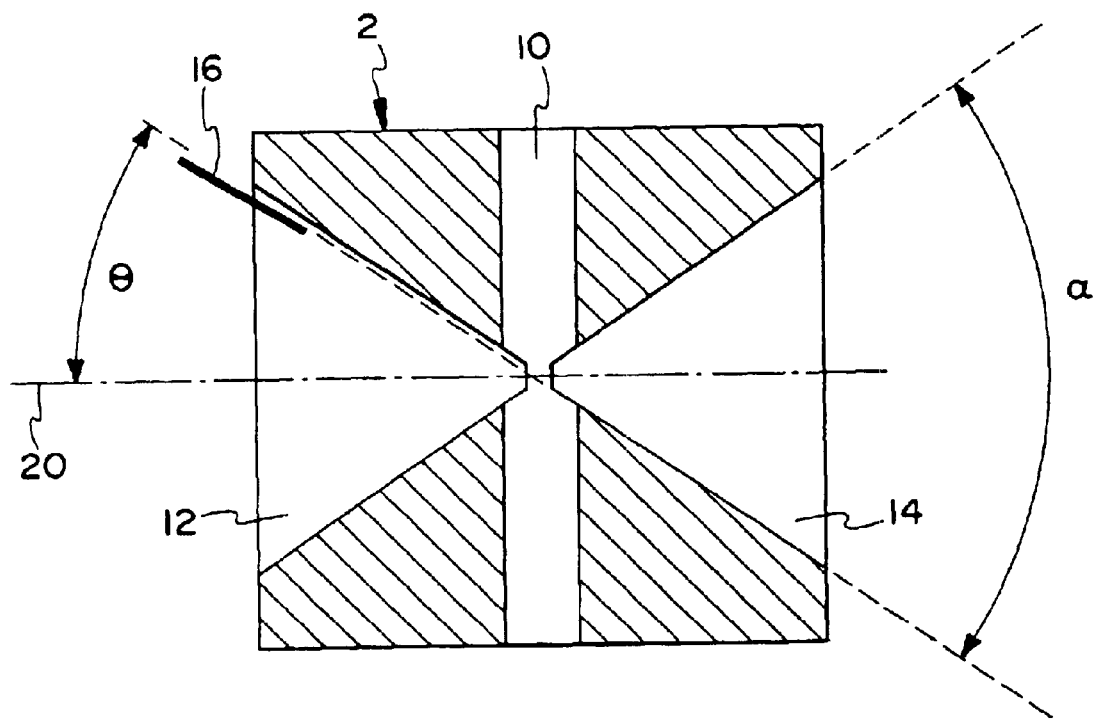
FIG. 4 depicts the angular relationship of various components of the apparatus depicted in FIG. 1.

Referring to FIGS. 1 to 3, an analyzing probe A is illustrated in one of many possible configurations. The details of the analyzing probe A are further shown in FIGS. 2 and 3. Referring to FIGS. 2 and 3, the analyzing probe A includes a body portion 2, a first end cap 4 and a second end cap 6. Preferably, the analyzing probe A has a substantially tubular housing. "Tubular" as used herein is defined a follows: a member having the form of a tube with a cross-section of any shape including but not limited circular, elliptical, square, rectangular, hexagonal, triangular, and other polygons. The body portion 2 includes a scattering chamber 8 and a fluid passageway 10. The scattering chamber 8 includes two cone-shaped portions 12 and 14. As seen in FIG. 4, cone-shaped portions 12 and 14 form an angle α at their base. The cone-shaped portions 12 and 14 are disposed on opposite sides of the fluid passageway 10. While the scattering chamber 8 is depicted as having two cone-shaped portions of equal size, it will be readily appreciated that the scattering chamber 8 may be configured in any suitable manner.

The analyzing probe A includes a plurality of transmitting optical fibers 16. As is readily evident from FIG. 2, the transmitting optical fibers are held in position by end cap 4. End cap 4 is in turn secured to body portion 2 by a plurality of screws 18. However, it will be readily appreciated that end cap 4 may be secured to body portion 2 in any conventional manner. Referring to FIG. 4, the transmitting optical fibers 16 form an angle θ with the longitudinal axis 20 of body portion 2. Preferably, angle θ is one half of angle α. In the most preferred form, angle θ forms a 30° angle with the longitudinal axis 20 of body portion 2. Where angle θ is 30°, angle α is preferably 60°. It will be readily appreciated that the orientation of the transmitting optical fibers may be varied depending upon the particular application.

The transmitting optical fibers 16 have first and second ends. The first ends 22 are disposed in or adjacent the scattering chamber 8. The second ends of the transmitting optical fibers are connected to a source of electromagnetic radiation (not shown). It will be readily appreciated that any conventional source may be used. Further, the wavelength of the electromagnetic radiation may be varied as desired. The preferred orientation of the transmitting optical fibers 16 focuses the electromagnetic radiation to approximately a single point without the need for a lens or series of lenses.

The end cap 6 is preferably threaded into an end of the body portion 2 opposite the end cap 4. An annular collar 24 is threaded into the end cap 6. It will be readily appreciated that the end cap 6 and the annular collar 24 may held in position by any conventional means. A collecting optical fiber 26 is held in position by annular collar 24. A first end 28 of the collecting optical fiber 26 is disposed adjacent the scattering chamber 8 in order to collect the electromagnetic radiation scattered by the particles in the fluid stream passing through fluid passageway 10. The second end of the collecting optical fiber 26 is connected to a processing unit employed to process the signal conveyed by the collecting optical fiber 26 to identify one or more characteristics of the particles in the fluid stream. The processing unit can be a photodiode or any conventional device.

FIGS. 5 Through 8

Figure 5:
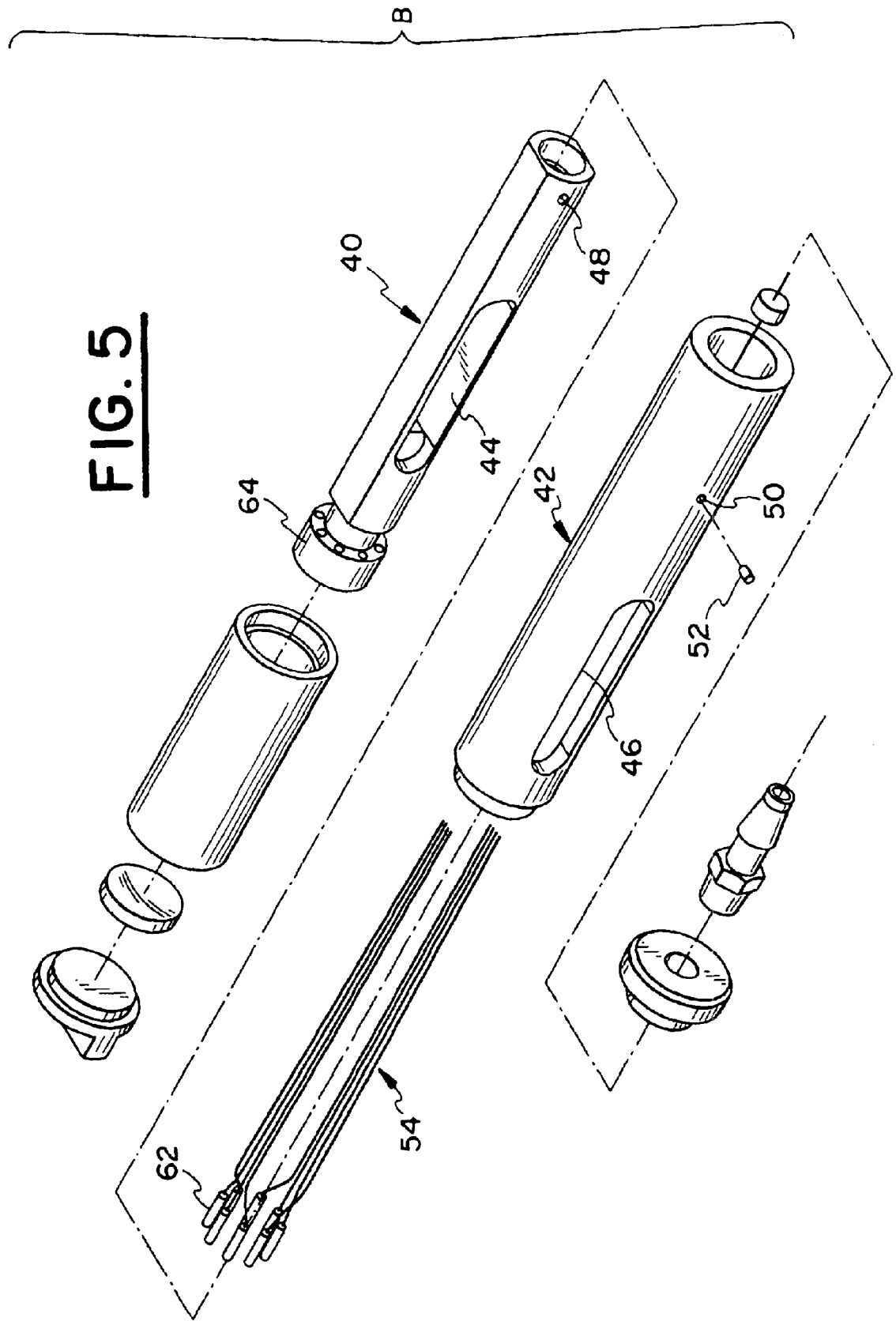
FIG. 5 is an exploded perspective view of an alterative form of the most preferred embodiment of the present invention.
Figures 6, 7:
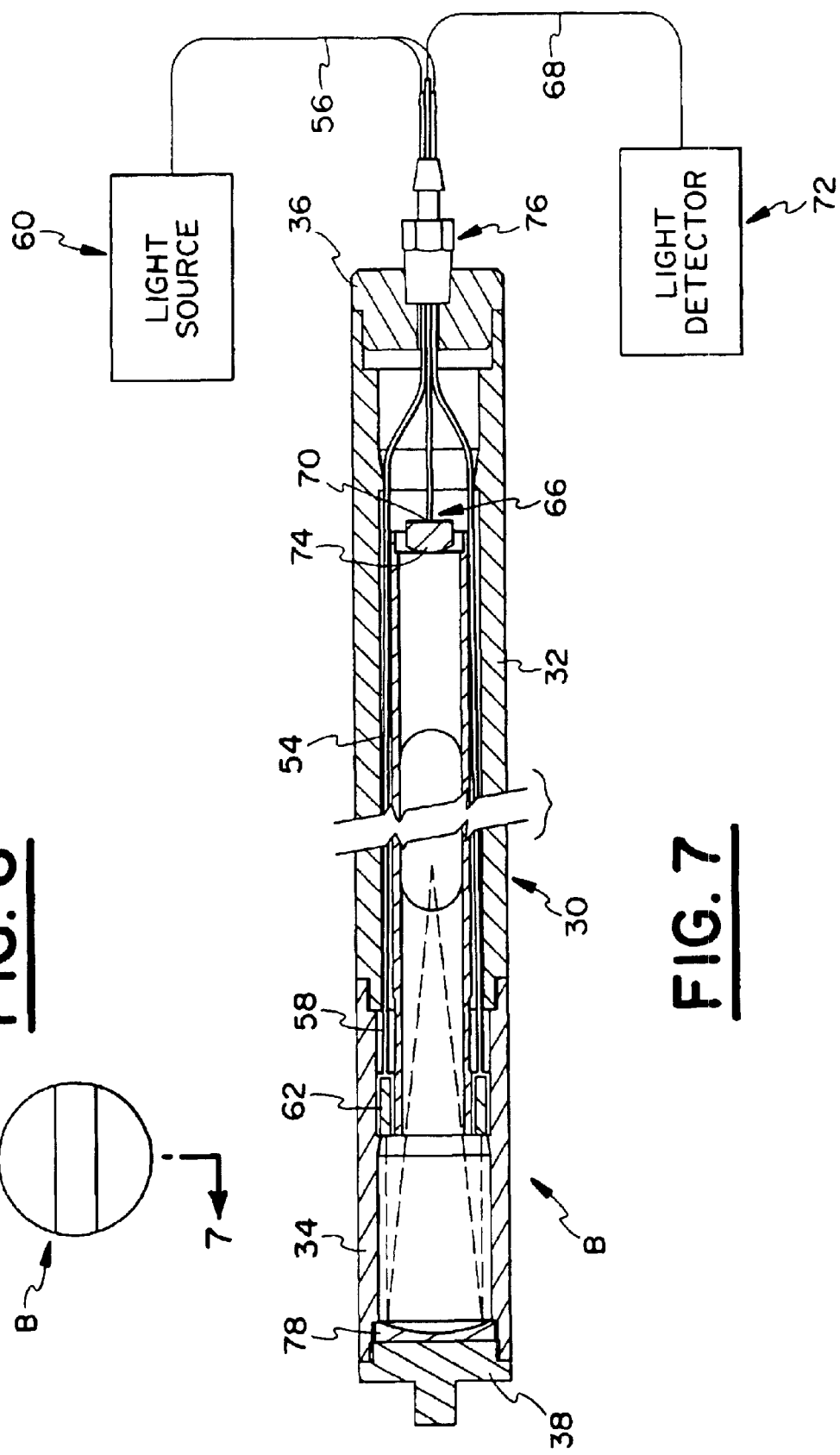
FIG. 6 is a side elevational view of the apparatus depicted in FIG. 5.
FIG. 7 is a cross-sectional view taken along lines 7—7 in FIG. 6.
Figure 8:
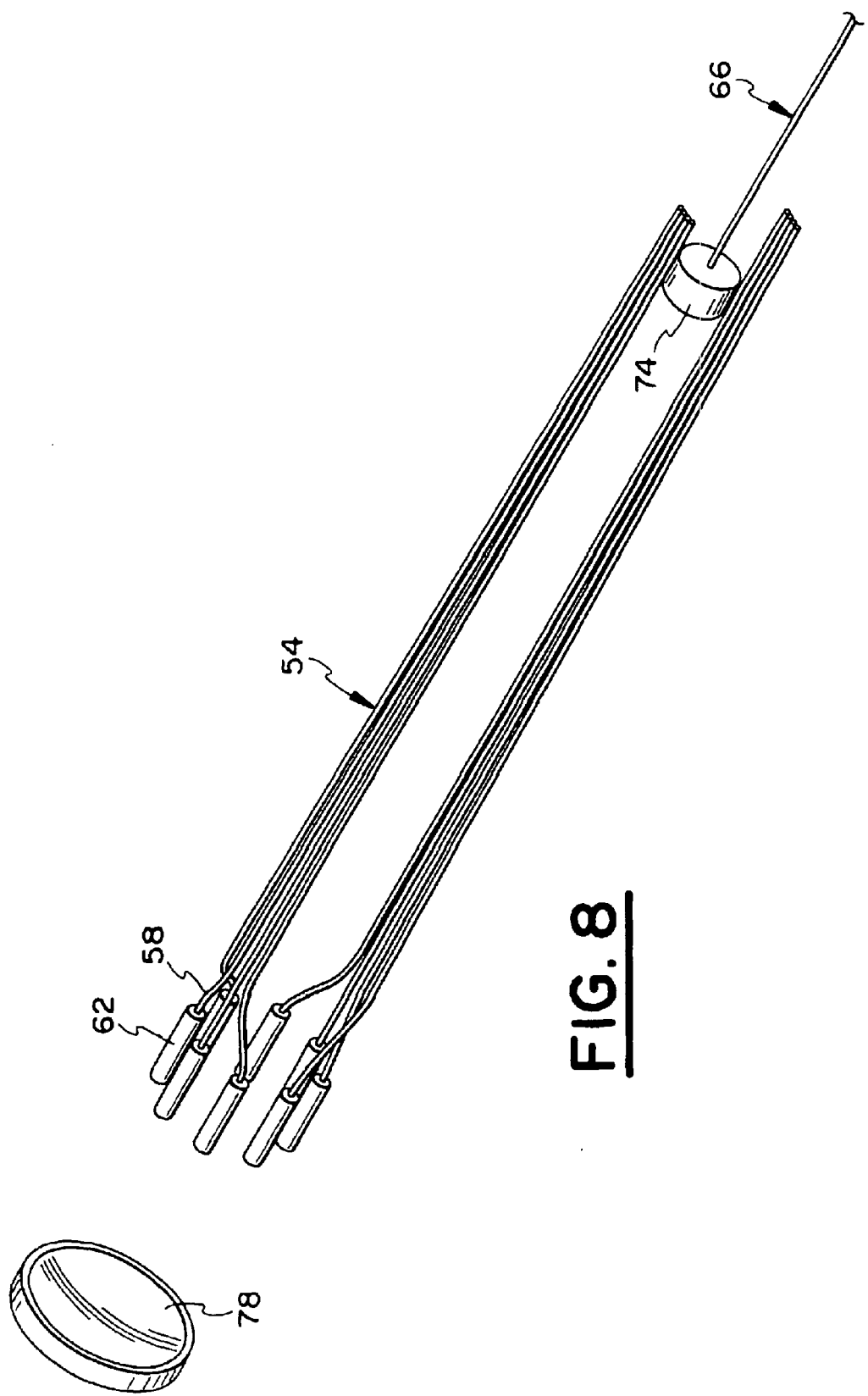
FIG. 8 is a perspective view of several components of the apparatus depicted in FIG. 5.

An alternative form of the most preferred embodiment of the present invention will now be described with reference made to FIGS. 5 to 8. Referring to FIGS. 5 to 7, analyzing probe B includes a substantially tubular housing 30. While housing 30 is preferably substantially tubular, it will be readily appreciated that housing 30 can take any desired configuration.

Referring to FIG. 7, housing 30 includes a first section 32, a second section 34, a first end cap 36 and a second end cap 38. Preferably, the adjoining ends of first section 32 and second section 34 are threaded so that the first section 32 can be readily connected to second section 34. However, it will be readily appreciated that first section 32 and second section 34 may be connected in any conventional manner. Further, housing 30 can be formed as a single piece rather than multiple sections or pieces. The first end cap 36 is threaded onto an end of first section 32. Similarly, the second end cap 38 is threaded onto an end of second section 34. However, it will be readily appreciated that the ends caps may be secured to the corresponding sections by any conventional means.

Referring to FIG. 5, the first section 32 includes an inner sleeve 40 and an outer sleeve or shell 42. Inner sleeve 40 has a scattering chamber 44 formed therein. Outer sleeve 42 includes a fluid passageway 46 in fluid communication with the scattering chamber 44. Inner sleeve 40 includes an opening 48. Similarly, outer sleeve or shell 42 includes an opening 50. An alignment pin 52 is inserted into openings 48 and 50 to align the scattering chamber 44 with the fluid passageway 46.

A plurality of transmitting optical fibers 54 are supported on the exterior surface of the inner sleeve 40. Preferably, eight (8) transmitting optical fibers are used. However, it will be readily appreciated that the number of optical fibers may be varied. The transmitting optical fibers 54 have first and second ends 56 and 58, respectively. First ends 56 are connected to a source 60 for generating electromagnetic radiation. It will be readily appreciated that any conventional source may be used to generate electromagnetic radiation of any desired wavelength. Each of the second ends 58 of the plurality of transmitting optical fibers 54 are provided with a collimator 62. As best seen in FIGS. 5 and 7, the collimators 62 are disposed in an alignment or orienting collar 64. The alignment collar 64 maintains the collimators 62 in the desired position.

At least one collecting optical fiber 66 extends into the first section 32 of housing 30. The collecting optical fiber 66 includes a first end 68 and a second end 70. First end 68 is connected to a detection device 72. Detection device 72 processes the signal collected by the collecting optical fiber 66 to determine one or more characteristics of the particles in the fluid stream being tested. The detection device 72 may be any conventional means for processing electromagnetic radiation including but not limited to a photodiode or a PMT. The second end 70 of collecting optical fiber 66 includes a collecting optical element such as a collimator 74. However, it will be readily appreciated that other optical collecting elements may be employed in place of collimator 74. A fitting 76 is threaded into the first end cap 36. Preferably, an outer protective casing (not shown) is connected to the exposed end of fitting 76 to protect the exposed portions of the transmitting optical fibers 54 and the collecting optical fiber 66, i.e., the transmitting and collecting optical fibers pass through the protective casing.

A concave mirror 78 is disposed in the second section 34 of housing 30. Electromagnetic radiation transmitted in parallel paths by the transmitting optical fibers 54 and the corresponding collimators 62 is redirected by the concave mirror 78 to a point in the scattering chamber 44 as shown in FIG. 7. It will be readily appreciated that optical elements other than a concave mirror may be used. A fluid stream to be tested is directed through fluid passageway 46 into the scattering chamber 44. The electromagnetic radiation is scattered by particles suspended in the fluid stream. The collecting optical fiber 66 collects the signal generated by the scattered electromagnetic radiation and conveys it to the detecting device for processing to determine at least one characteristic of the particles in the fluid stream.

While this invention has been described as having a preferred design, it is understood that the preferred design can be further modified or adapted following in general the principles of the invention and including but not limited to such departures from the present invention as come within the known or customary practice in the art to which the invention pertains. The claims are not limited to the preferred embodiment and have been written to preclude such a narrow construction using the principles of claim differentiation.

We claim:

1. An apparatus for analyzing a stream of fluid, comprising:
   (a) an analyzing probe adapted to analyze a stream of fluid, said analyzing probe having a substantially tubular housing, said substantially tubular housing having a longitudinal axis and an exterior surface;
   (b) a scattering chamber and a fluid passageway, said fluid passageway being in fluid communication with said scattering chamber to direct a stream of fluid to be tested into said scattering chamber, said scattering chamber being disposed in said substantially tubular housing, at least a portion of said fluid passageway extends at a first angle to said longitudinal axis and between said exterior surface of said substantially tubular housing and said scattering chamber;
   (c) at least one transmitting optical fiber to transmit electromagnetic radiation to said scattering chamber, said at least one transmitting optical fiber having first and second ends, said second end being connected to a source; and,
   (d) at least one collecting optical fiber for collecting electromagnetic radiation from said scattering chamber for analysis, said at least one collecting optical fiber having first and second ends, said second end being connected to a detection device, said first end of said at least one collecting optical fiber being offset along said longitudinal axis from said first end of said at least one transmitting optical fiber.

2. An apparatus for analyzing a stream of fluid, comprising:
   (a) an analyzing probe adapted to analyze a stream of fluid, said analyzing probe having a substantially tubular housing, said substantially tubular housing having a longitudinal axis and an exterior surface;

(b) a scattering chamber and a fluid passageway, said fluid passageway being in fluid communication with said scattering chamber to direct a stream of fluid to be tested into said scattering chamber, said scattering chamber being disposed in said substantially tubular housing, at least a portion of said fluid passageway extends at a first angle to said longitudinal axis and between said exterior surface of said substantially tubular housing and said scattering chamber;

(c) at least one transmitting optical fiber to transmit electromagnetic radiation to said scattering chamber;

(d) at least one collecting optical fiber for collecting electromagnetic radiation from said scattering chamber for analysis, and;

(e) a plurality of transmitting optical fibers, said transmitting optical fibers are disposed at a second angle to said longitudinal axis such that electromagnetic radiation transmitted by said plurality of transmitting optical fibers is directed to approximately the same point in said scattering chamber thereby obviating the need for a lens for focusing the electromagnetic radiation to approximately a single point.

3. An apparatus as set forth in claim 2, wherein:
(a) said second angle is less than 90° and said first angle is approximately 90°.

4. An apparatus as set forth in claim 1, wherein:
(a) said scattering chamber includes at least one cone-shaped portion, said cone-shaped portion forms an angle less than 90°; and,
(b) a plurality of transmitting optical fibers, said transmitting optical fibers are disposed at an angle less than 90° to said longitudinal axis such that electromagnetic radiation transmitted by said plurality of transmitting optical fibers is directed to approximately the same point in said scattering chamber thereby obviating the need for a lens for focusing the electromagnetic radiation to approximately a single point.

5. An apparatus as set forth in claim 4, wherein:
(a) said transmitting optical fibers are disposed at approximately a 30° angle to said longitudinal axis and said cone-shaped portion forms approximately a 60° angle.

6. An apparatus a set forth in claim 1, wherein:
(a) said substantially tubular housing includes first and second end caps and a body portion, said first and second end caps are secured to opposite ends of said body portion; and,
(b) said at least one transmitting optical fiber extends outwardly from said first end cap; and,
(c) said at least one collecting optical fiber extends outwardly from said second end cap.

7. An apparatus as set forth in claim 1, wherein:
(a) said scattering chamber has first and second cone-shaped portions; and,
(b) at least a portion of said fluid passageway is disposed between said first cone-shaped portion and said second cone-shaped portion.

8. An apparatus as set forth in claim 1, wherein:
(a) said fluid passageway extends at approximately a 90° angle to said longitudinal axis.

9. An apparatus for analyzing a stream of fluid, comprising:
(a) an analyzing probe adapted to analyze a stream of fluid, said analyzing probe including a housing having a longitudinal axis;

(b) said analyzing probe further including a scattering chamber and a fluid passageway, said fluid passageway being in fluid communication with said scattering chamber to direct a stream of fluid to be tested into said scattering chamber;

(c) at least first and second transmitting optical fibers to transmit electromagnetic radiation to said scattering chamber, said first and second transmitting optical fibers being disposed at an angle to said longitudinal axis such that electromagnetic radiation transmitted by said first and second transmitting optical fibers is directed to approximately the same point in said scattering chamber thereby obviating the need for a lens for focusing the electromagnetic radiation to approximately a single point; and, (d) at least one collecting optical fiber for colleting electromagnetic radiation from said scattering chamber for analysis.

10. An apparatus as set forth in claim 9, wherein:
(a) said collecting optical fiber extends along said longitudinal axis of said housing.

11. An apparatus as set forth in claim 9, wherein:
(a) said scattering chamber includes first and second cone-shaped portions forming first and second angles, said first and second angles being less than 90°.

12. An apparatus as set forth in claim 9, further including:
(a) at least three transmitting optical fibers disposed at an angle to said longitudinal axis.

13. An apparatus as set forth in claim 12, wherein:
(a) said at least three transmitting optical fibers are disposed at approximately a 30° angle to said longitudinal axis.

14. An apparatus for analyzing a stream of fluid, comprising:
(a) an analyzing member adapted to be inserted into a hazardous environment to analyze a stream of fluid, said analyzing member including a housing;
(b) a scattering chamber and a fluid passageway, said fluid passageway being in fluid communication with said scattering chamber to direct a stream of fluid to be tested into said scattering chamber, said scattering chamber being disposed in said housing;
(c) at least one transmitting optical fiber to transmit electromagnetic radiation to said scattering chamber;
(d) at least one collecting optical fiber for collecting electromagnetic radiation from said scattering chamber for analysis; and
(e) a reflecting member disposed in said housing for redirecting electromagnetic radiation transmitted by said at least one transmitting optical fiber to said scattering chamber, said at least one transmitting optical fiber being disposed closer to said reflecting member than said at least one collecting optical fiber.

15. An apparatus as set forth in claim 14, wherein:
(a) said fluid passageway extends through at least a portion of said housing of said analyzing member.

16. An apparatus as set forth in claim 15, wherein:
(a) said transmitting optical fiber has first and second ends, said first end is connected to a source of electromagnetic radiation and said second end is disposed adjacent said reflecting member.

17. An apparatus as set forth in claim 16, wherein:
(a) said collecting optical fiber has first and second ends, said first end is connected to a device for detecting electromagnetic radiation and said second end is disposed in said housing.

18. An apparatus as set forth in claim 17, wherein:
(a) said scattering chamber is positioned between said second end of said collecting optical fiber and said second end of said transmitting optical fiber.

19. An apparatus as set forth in claim 14, wherein:
(a) said housing has first and second sections, said scattering chamber is disposed in said first section and said reflecting member is disposed in said second section.

20. An apparatus as set forth in claim 19, wherein:
(a) said first section includes an inner sleeve and an outer shell, said scattering chamber is formed in said inner sleeve, said fluid passageway is formed in said outer shell.

21. An apparatus for analyzing a stream of fluid, comprising:
(a) an analyzing member adapted to be inserted into an environment to analyze a stream of fluid, said analyzing member having a longitudinal axis, said analyzing member including a substantially tubular housing having first and second sections, said first section includes an inner member and an outer member, at least a portion of said inner member overlapping said outer member along said longitudinal axis;
(b) a scattering chamber and a fluid passageway, said fluid passageway being in fluid communication with said scattering chamber to direct a stream of fluid to be tested into said scattering chamber, said scattering chamber being formed in one of said first and second sections of said housing;
(c) a plurality of transmitting optical fibers to transmit electromagnetic radiation to said scattering chamber; and,
(d) at least one collecting optical fiber for colleting electromagnetic radiation from said scattering chamber for analysis.

22. An apparatus as set forth in claim 21, further including:
(a) a reflecting member disposed in said housing for redirecting electromagnetic radiation transmitted by said at least one transmitting optical fiber to said scattering chamber.

23. An apparatus as set forth in claim 22, wherein:
(a) said reflecting element is disposed in said second section of said substantially tubular housing and redirects electromagnetic radiation to said first section of said substantially tubular housing.

24. An apparatus as set forth in claim 21, wherein:
(a) said plurality of transmitting optical fibers are supported on an exterior surface of said inner member.

25. An apparatus as set forth in claim 24, wherein:
(a) each of said transmitting optical fibers include a collimator.

26. An apparatus as set forth in claim 25, wherein:
(a) said collimators are disposed in an annular collar.

27. An apparatus as set forth in claim 26, wherein:
(a) said annular collar is disposed in said second section of said housing.

28. An apparatus for analyzing a stream of fluid, comprising:
(a) an analyzing member adapted to be inserted into an environment to analyze a stream of fluid, said analyzing member including a substantially tubular housing having first and second sections, said first section includes an inner member and an outer member;
(b) a scattering chamber and a fluid passageway, said fluid passageway being in fluid communication with said scattering chamber to direct a stream of fluid to be tested into said scattering chamber, said scattering chamber being formed in one of said first and second sections of said housing;
(c) a plurality of transmitting optical fibers to transmit electromagnetic radiation to said scattering chamber;
(d) at least one collecting optical fiber for collecting electromagnetic radiation from said scattering chamber for analysis
(e) said plurality of transmitting optical fibers extend in said first and second sections of said substantially tubular housing.

29. An apparatus as set forth in claim 28, wherein:
(a) said collecting optical fiber has first and second ends, said first end is connected to a detecting device for detecting electromagnetic radiation, said second end is disposed in said first section of said housing.

30. An apparatus as set forth in claim 21, wherein:
(a) said substantially tubular housing includes first and second end caps;
(b) said plurality of transmitting optical fibers extend through said first end cap; and,
(c) said collecting optical fiber extends through said first end cap.

31. An apparatus for analyzing a stream of fluid, comprising:
(a) an analyzing member adapted to be inserted into an environment to analyze a stream of fluid, said analyzing member including a substantially tubular housing having first and second sections, said first section being detachably connected to said second section;
(b) a scattering chamber and a fluid passageway, said fluid passageway being in fluid communication with said scattering chamber to direct a stream of fluid to be tested into said scattering chamber, said scattering chamber being formed in one of said first and second sections of said housing;
(c) at least one transmitting optical fiber to transmit electromagnetic radiation to said scattering chamber; and,
(d) at least one collecting optical fiber for colleting electromagnetic radiation from said scattering chamber for analysis.

32. An apparatus for analyzing a stream of fluid, comprising:
(a) an analyzing member for analyzing a stream of fluid, said analyzing member including a housing;
(b) a scattering chamber and a fluid passageway, said fluid passageway being in fluid communication with said scattering chamber to direct a stream of fluid to be tested into said scattering chamber, said scattering chamber being disposed in said housing;
(c) first and second transmitting optical fibers to transmit electromagnetic radiation to said scattering chamber;
(d) at least one collecting optical fiber for collecting electromagnetic radiation from said scattering chamber for analysis; and
(e) a focusing member for focusing the electromagnetic radiation transmitted by said first and second optical fibers to a focal point, said focal point being located in said scattering chamber, said focal point further being removed from said first and second transmitting optical fibers and said collecting optical fiber.

* * * * *